United States Patent [19]
Brailly et al.

[11] Patent Number: 5,559,012
[45] Date of Patent: Sep. 24, 1996

[54] THERAPEUTIC, IL-6 ANTIBODY KITS, AND PROCESS FOR THEIR PREPARATION

[75] Inventors: Hervé Brailly, Aix En Provence Boûches du Rhône; Félix A. Montero-Julian, Marseille Boûches du Rhône; Bernard Klein, Vertou Loire-Atlantique, all of France

[73] Assignee: Immunotech, Marseille, France

[21] Appl. No.: 280,230

[22] Filed: Jul. 25, 1994

[30] Foreign Application Priority Data

Jul. 23, 1993 [FR] France .................................. 93 09382

[51] Int. Cl.⁶ .............................. C12P 21/08; C12N 5/12; C07K 16/24
[52] U.S. Cl. .................... 435/70.21; 435/240.27; 530/388.23
[58] Field of Search ................ 530/388.23; 435/70.21, 435/240.27

[56] References Cited

FOREIGN PATENT DOCUMENTS 0410813 1/1991 European Pat. Off. .
9201472 2/1992 WIPO .

OTHER PUBLICATIONS

Wÿdenes, J. et al., Molecular Immunology, 28(11):1183–1192, 1991.

Osband, M. E. et al., Immunology Today, 11(6):193–195, 1990.

Waldmann, T. A., Science, 252:1657–1662, Jun. 1991.

Winter, G. et al., TIPS, 14:139–143, May 1993.

Research In Immunology. vol. 143, No. 7, 1992, Paris, France. pp. 774–776. B. Klein et al. "Clinical Applications of IL–6 Inhibitors".

*Primary Examiner*—Marian C. Knode
*Assistant Examiner*—Susan A. Loring
*Attorney, Agent, or Firm*—Browdy and Neimark

[57] ABSTRACT

A therapeutic kit which includes at least three unlinked monoclonal antibodies for neutralizing a short life IL-6 cytokine and a method for preparing said kit.

10 Claims, 10 Drawing Sheets

FIGURE 3B
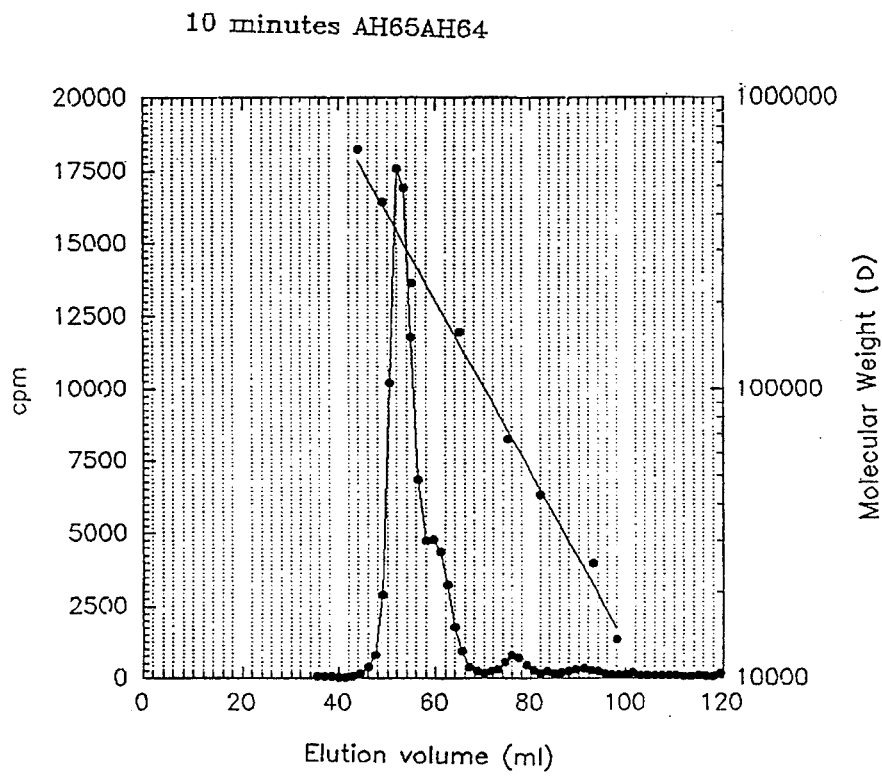
10 minutes AH65AH64
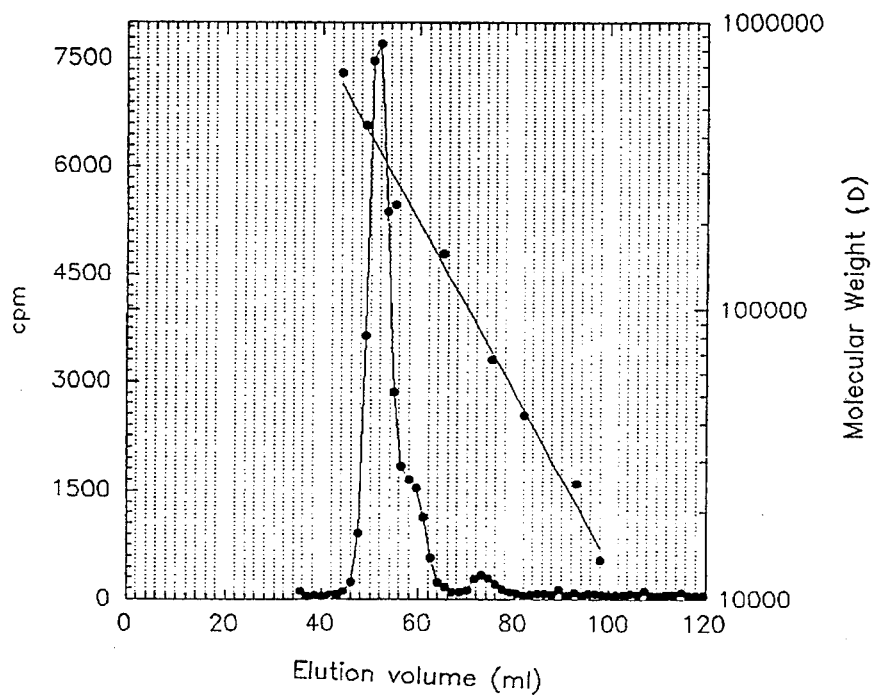
FIGURE 3C

FIGURE 4B
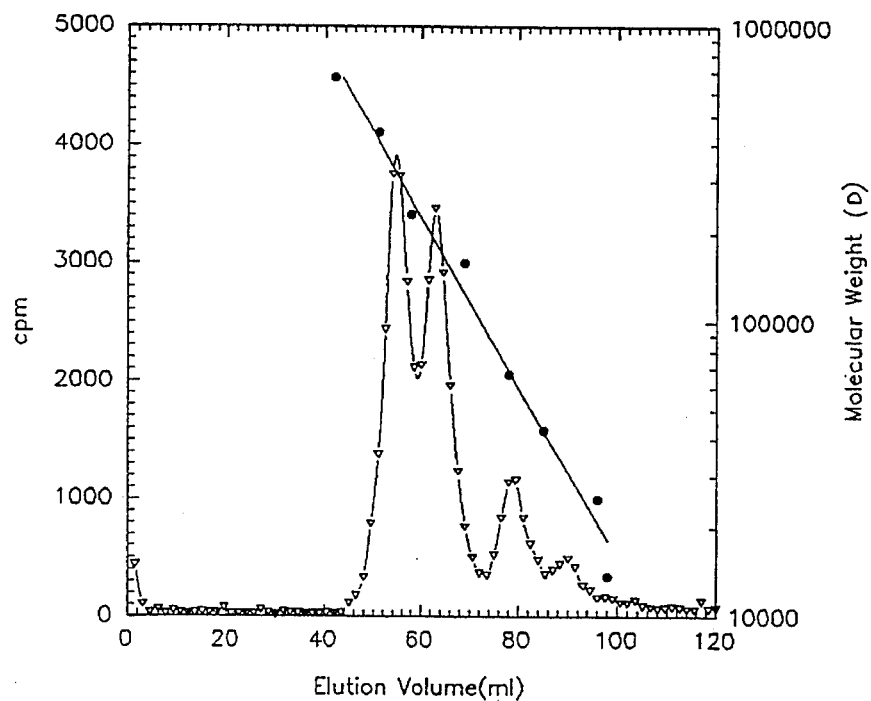
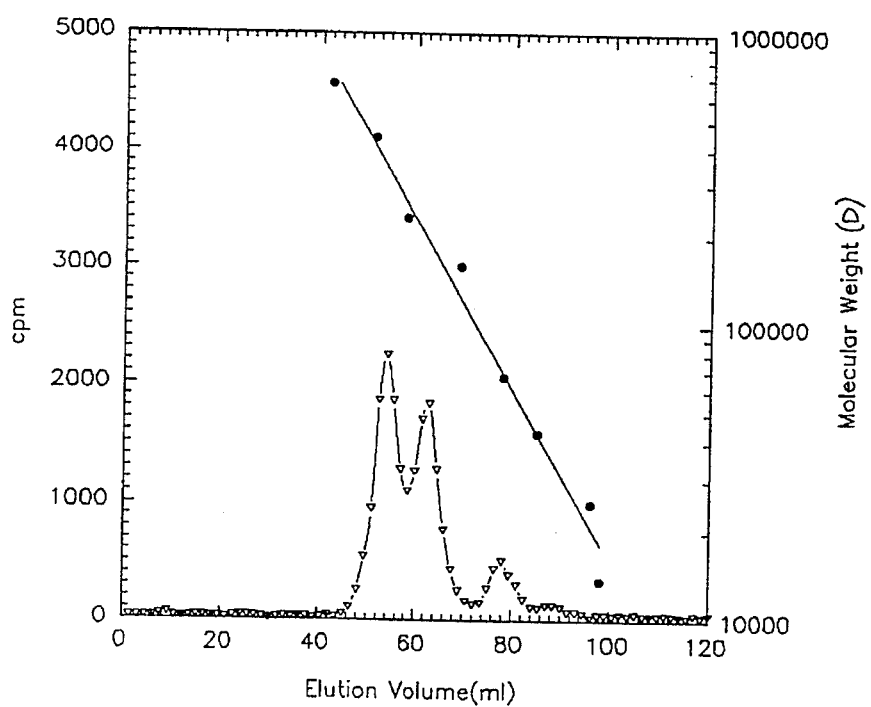
FIGURE 4C

FIGURE 5B
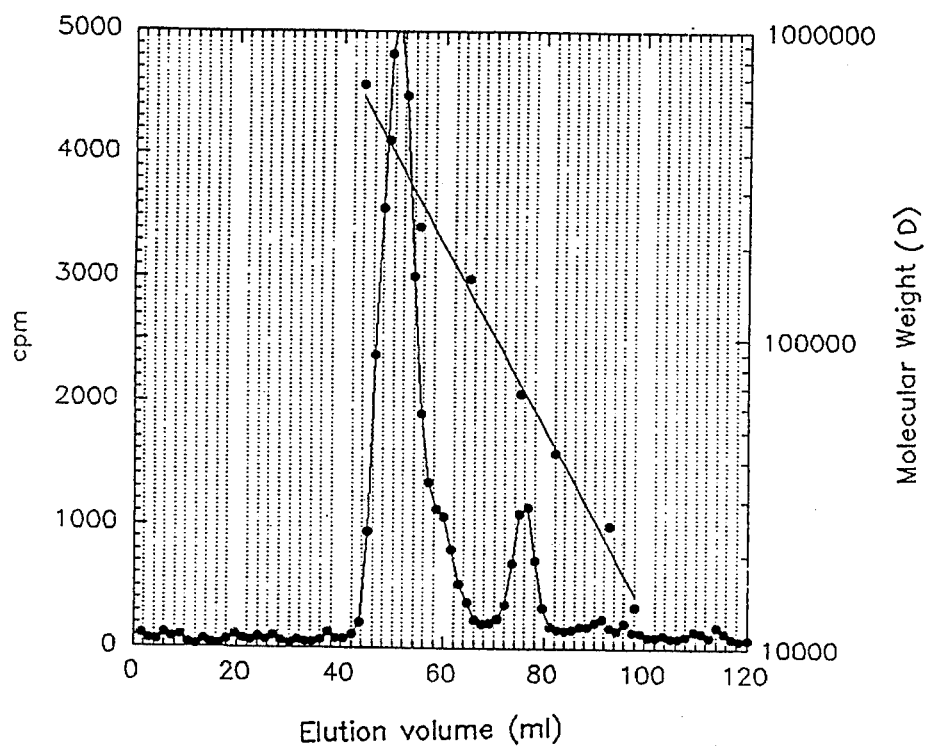
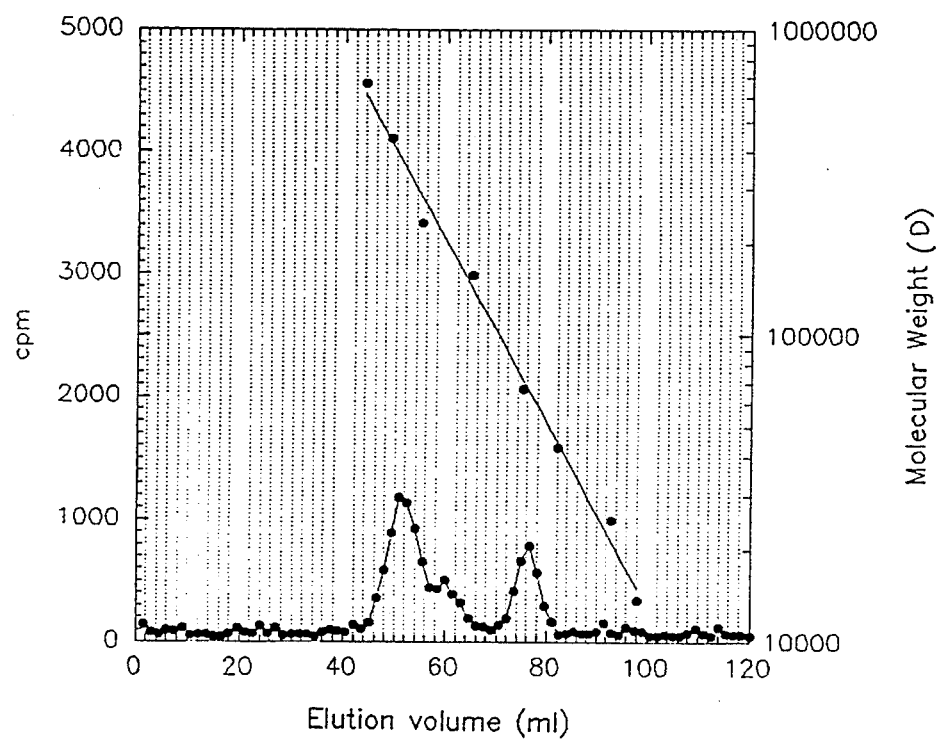
FIGURE 5C

THERAPEUTIC, IL-6 ANTIBODY KITS, AND PROCESS FOR THEIR PREPARATION

The present application concerns new therapeutic, antiproteic mediator kits, a process for their preparation and pharmaceutical compositions containing them.

Interleukin 6 (IL-6) is involved in many pathological processes. Specifically, IL-6 is the principal in vivo growth factor for several tumors including multiple myeloma and monoblastic acute leukemia. It is a growth factor for many other tumors including renal carcinoma and Kaposi's sarcoma. IL-6 is the chief mediator which, in vivo, induces the synthesis of the acute phase proteins in the hepatocytes and is in this manner involved in the acute systemic inflammatory response during septic shocks. IL-6 participates in the induction of the terminal differentiation and the production of immunoglobulins by B lymphocytes and is thus involved in the oligoclonal activation and the hyperglobulinemia observed in autoimmune diseases affecting the B compartment, such as rheumatoid arthritis and in HIV infections.

For all these reasons, it would be desirable to have methods and products to antagonize the in vivo activity of IL-6.

Different approaches have been described to attain this aim.

Several immunosuppressive and anti-inflammatory drugs inhibit the synthesis of cytokine type mediators. However, these agents do not block selectively the activity of only one mediator.

A more selective approach consists in blocking the interleukin-6 receptor with a specific antagonist. A monoclonal antibody, binding the IL-6 receptor (IL-6R) competitively with IL-6 has been described in EP-A-0409607. However, the IL-6 receptor (IL-6R) occurs in circulating soluble form at high concentration in the serum and is widely distributed in the tissues, being expressed particularly in the hepatocytes. These two facts limit a priori the efficacy and specificity of a treatment with an anti-IL-6R antibody.

Another possibility consists of using an agent that binds IL-6 and prevents it from binding to its membrane receptor. Several monoclonal anti-IL-6 antibodies, utilizable for human therapy have been described (see, for example, DE-A-3939706). One of these has been employed in a clinical assay for the treatment of a terminal phase plasmablastic leukemia (Klein, B. et al., "Murine anti-interleukin-6 monoclonal antibody therapy for a patient with plasma cell leukemia" Blood 78: 1198, 1991). This assay showed that IL-6 controlled effectively tumor proliferation. However the patient resisted treatment since IL-6 accumulated in the circulation in the form of immune complexes with anti-IL-6 antibodies.

WO-A-92 01472 discloses the use of multivalent immunoglobulin complexes wherein the immunoglobulins are linked together, and their use for neutralizing the activity of cytokines in man, and particularly multimeric immunoglobulins. The number of immunoglobulins in such complexes is limited by solubility considerations.

The present invention provides a product, capable of blocking selectively a cytokine, preferably IL-6, in vivo, by means of agents binding the said cytokine, avoiding, for example, in the case of IL-6, the accumulation of the latter in the form of immune complexes with in vivo residence time much greater than that of free IL-6, and in a more general way, capable of blocking certain proteic mediators.

This is why one aspect of the present invention is a therapeutic kit for neutralizing a short life proteic mediator of sufficient size to have at least three antibody binding sites, wherein said kit includes at least three individual antibodies recognizing three distinct epitopes of the said proteic mediator, at least one of the said three antibodies blocking the biological activity of the said proteic mediator.

BRIEF DESCRIPTION OF THE DRAWINGS

FIGS. 3B and 3C show molecular sieve fractionation of plasma samples.

FIGS. 4B and 4C show the molecular sieve fractionation of plasma samples.

FIGS. 5B and 5C show the molecular sieve fractionation of plasma samples.

Figure 1A:
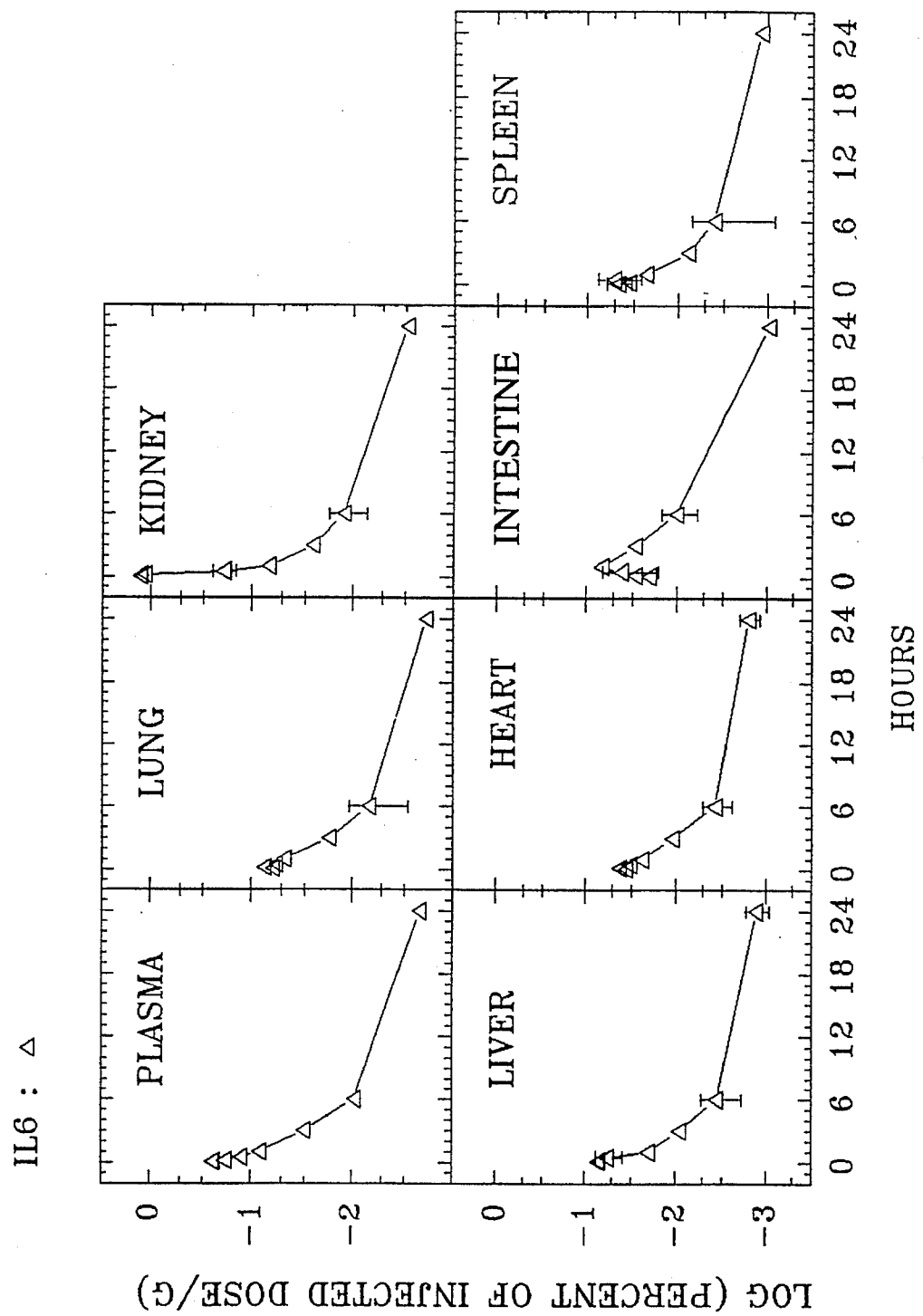
FIG. 1A shows the pharmacokinetics of radiolabeled human IL-6 in non-treated Balb/c mice.

By "proteic mediator with a short life time", is meant, in particular, circulating glycoproteic or proteic mediators, especially cytokines, such as IL-1, IL-2, IL-4, IL-5, IL-6, IL-7, IL-9, IL-10, IL-11, oncostatin-M, hemopoietic growth factors, such as G-CSF, GM-CSF, M-CSF, SCF and especially IL-6.

These mediators are sufficiently large to comprise at least three distinct, functional antibody sites.

By "kit" is meant not only the combination of individual antibodies in the same container, but also the association of antibodies in separate individual containers. The kit comprises preferably additionally instructions for the use of the antibodies.

In order to select the antibodies and corresponding mediators according to the invention, one can investigate the inhibitory ability of the antibodies on the mediator and verify that the said, at least three antibodies are active at different sites. Such experiments are described below in the experimental part.

Surprisingly, whereas the plasma half-life of a complexed mediator, e.g. IL-6, is essentially unchanged, approximately 12 to 24 hours, irrespective of the use of either only one or of two antibodies, provided that one, or at least one, of the two antibodies blocks the activity of the said mediator, the plasma half-life of the same mediator, complexed with a mixture of three antibodies, according to the invention, is analogous to that of the free mediator, i.e. of the order of 20 minutes.

Whereas it is sufficient that one of the said at least three antibodies, according to the invention, is capable of blocking the function of the proteic mediator, it is preferable that two of the said at least three antibodies are endowed with this property.

The antibodies used according to the present invention are an association of several, preferably monoclonal, antibodies.

The antibodies employed are preferably of the isotype. Normally mouse, rat or human IgG, and preferably, mouse IgG2a or human IgG1, type antibodies are used. The latter two types are preferred in view of the higher affinity of these antibodies for the constant part (Fc) of the immunoglobulins of the cellular receptors (FcRI receptors).

The antibodies employed should have an affinity for the antigen above $10^9$ liter/mole and preferably an affinity above 10 liter/mole.

The antibodies employed in the present invention may be of animal, particularly murine, origin, but preferably, are completely or partially humanized by, for example, one of the techniques such as described by G. Winter and C. Milstein in "Man-made antibodies", Nature Vol. 349, pages 293–299. When partially humanized, at least their Fc moiety is humanized. The therapeutic use of humanized antibodies leads to a reduction of the immunogenicity of the injected product. This may be an advantage for repeated or prolonged treatments. It is especially advantageous to use chimeric antibodies, whose Fc moieties come from a human type IgG1 antibody, thus at the same time decreasing the immunogenicity of the injected product and benefitting from the greater affinity of these antibodies for the human Fc receptors.

Consequently, one main application of the invention consists of a kit containing either one or several, preferably mouse or rat monoclonal antibodies, modified by genetic engineering so as to include a peptide sequence derived from an antibody of human origin. An example of such an embodiment according to the invention, consists of a kit containing either one or several hybrid antibodies comprising a fragment binding the antigen whose origin is a mouse or rat monoclonal antibody, and at least one part binding to the receptor of the Fc fragment of human origin. Another type of implementation of the invention consists of a kit according to the invention, containing either one or several antibodies of human origin, obtained from human B lymphocyte clones, or obtained by in vivo recombination of the genes of the human immunoglobulin repertoire.

The mixtures of antibodies, according to the invention, are, for example, those constituted by the following associations:

BE 4, BE 8 and AH65, BE4, AH64 and AH65, and
BE 4, BE 8, AH64 and AH65.

Hybridomas BE 4 and BE 8 were deposited in the Collection Nationale de Culture de Microorganismes "(CNCM)" Institut Pasteur, 28, rue du Dr Roux, Paris on Nov. 22, 1989 with the numbers 1-911 and 1-913, respectively.

Hybridomas AH64 and AH65 were deposited in the Collection Nationale de Culture de Microorganismes of Paris on Jul. 13, 1993 with the numbers 1-1333 and 1-1334, respectively.

A description of antibodies BE 4, BE 8, AH 64 and AH65 is provided later in the experimental part.

The present application concerns also a process for the preparation of associations or kits of antibodies, such as described above, comprising associating at least three antibodies which recognize three distinct epitopes of the said proteic mediator, at least one of the said three antibodies blocking the biological activity of said proteic mediator.

This association, as was seen, may concern either the mixture of the individual antibodies in the same container or the antibodies may be in separate containers, combined in one package, with, preferably, an instruction manual for their use.

Under advantageous conditions for the implementing the above process, the preferred choices of mediators and antibodies apply equally.

The above associations or therapeutic kits are endowed with remarkable properties. They are notably capable of antagonizing the activity of the mediator against which they are directed, in man or animals, such that the treated individual does not become resistant to the treatment, i.e. such that the treatment continues to yield beneficial effects without the accumulation of immune complexes.

The above properties are illustrated later in the experimental part and justify the use of the above antibody associations as a drug.

This is why the present application has further as object medicaments consisting of the kits or associations of antibodies described above.

These medicaments are used, for example, to act on mediators of which it would be advantageous to inhibit the in vivo activity under different pathological conditions. In particular, this method may be employed profitably in two types of pathological situations :a) in the case of the chronic low-level production of a cytokine-type molecule, normally not detectable in the circulation and b) in the case of the massive, acute production of a cytokine-type molecule.

One embodiment of the invention thus consists of using the association of the above antibodies described to block the action of a cytokine which favors the growth of a tumor.

Major applications are the in vivo inhibition of IL-1, IL-6 and of GM-CSF in malignant blood disorders such as acute myeloid leukemia, B-cell lymphoma and multiple myeloma and of IL-2, IL-7 and IL-9 in T-cell lymphomas. In particular, an important embodiment consists of the in vivo inhibition of the action of IL-6 on multiple myeloma for which IL-6 is an essential proliferation factor.

Another important method of use consists of the in vivo inhibition of the action of IL-4 and IL-5 in Hodgkin's lymphoma.

Other applications of the invention concern the inhibition of cytokine-type mediators in solid tumors where proliferation is favored by the mediator. Major applications, in particular, comprise in the in vivo inhibition of the action of IL-6 in Kaposi's sarcoma. Another major method of use comprises in blocking the action of oncostatin-M in Kaposi's sarcoma. In acute situations, it is necessary to block and to eliminate rapidly the mediator, whose action should be inhibited. Consequently, the method described applies especially to such situations. One application considered consists of the inhibition of IL-1 and IL-6 in septicemias. An important method of use consists in the in vivo inhibition of the action of IL-5 in the hypereosinophilia syndromes. An especially important application consists of the inhibition of the action of IL-6, massively produced during episodes of sepsis which affect patients suffering from a tumor whose growth is favored by IL-6, as in the case especially in multiple myeloma, and in different malignant blood disorders, mentioned previously, as well as for AIDS patients with Kaposi's syndrome.

These applications are cited only by way of illustration in view of the variety of short-life proteic mediators at the origin of a variety of pharmacological activities, targeted by the invention.

This is why the present application has also as object a method of antagonizing the activity of a short-life proteic mediator of sufficient size to include at least three antibody sites, wherein an association of at least three antibodies recognizing three distinct epitopes of the said protein mediator is used, at least one of the said three antibodies being in sufficient amount to block (or neutralize) the biological activity of the said proteic mediator.

In a preferred embodiment of the method described above, primarily the associations described above are used to antagonize the mediators, also described above, notably to fight against the various pathological conditions previously mentioned.

The present invention has also as object the pharmaceutical compositions characterized in that they include at least one of the drugs described above.

Generally speaking, the pharmaceutical compositions primarily utilizable, are injectable preparations. The antibodies may be kept in liquid or solid form, for example in lyophilized form. The major application is that for which the three antibodies are in the same vial. In another embodiment, the three antibodies to be injected are in three separate vials. In all the applications of the invention, the three antibodies may be combined in the pharmaceutical compositions with one or several other active principles as well as with useful adjuvants bearing on the pharmacodynamic properties of that composition.

The usual dose, varying according to the patient treated, the disease concerned and the characteristics of the antibodies constituting the injected combination, may range, for example, from 1 to 25 mg per day, administered intravenously in man for the combination (BE 4+BE 8+AH65) and administered daily for 10 to 20 days during a sepsis episode in a patient suffering from multiple myeloma.

The following examples illustrate the present invention, without, however, being limiting.

1. ANTI IL-6 ANTIBODIES

Monoclonal anti-cytokine antibodies can be obtained by the immunization of mice of various strains (e.g. Balb/c or DBA2) with partially or completely purified human recombinant cytokines and fusion of the spleens of the immunized mice with a murine myeloma of the X63 type, according to conventional procedures. It is preferable to select the anti-cytokine antibody-producing hybridomas employing the purified cytokine. The utilizable antibodies of a therapeutic kit, such as described in the present invention, must, furthermore, have certain special properties, i.e. (1) the ability of at least three of these antibodies to bind simultaneously to IL-6; (2) the capacity of at least one of these antibodies to block the biological activity of IL-6. The experimental procedures permitting the selection of antibodies according to these two criteria are described below.

The mouse monoclonal antibodies utilized in the examples below are designated as BE 8, BE 4, AH64 and AH65, respectively. The hybridomas producing antibodies BE 4 and BE 8 have been deposited and registered in Paris at the Collection Nationale de Culture de Microorganismes (CNCM) on Nov. 27, 1989 with the numbers BE8: CNCM. No. 1/913; BE4: CNCM. No. 1/911. The purified antibodies were obtained commercially at the CTS of Besangon (France). A complete description of these antibodies is provided in EP-A-0430193 and DE-A-3939706. The purified antibodies are kept sterile at +4° C.

In the case of the antibodies designated as AH64 and AH65, the corresponding hybridomas (D801D6M and D8812D3M, respectively) were cultivated according to conventional techniques. The antibodies are produced in the ascites of nu/nu mice and then purified on a protein A (Pharmacia) column, according to current methods. The solutions of purified antibodies are finally diluted in an isotonic 0.9 g/l saline solution, sterilized by filtration at 0.22 µm and stored at +4° C. The hybridomas producing antibodies AH64 and AH65 were deposited and registered in Paris at the Collection Nationale de Culture de Microorganismes (CNCM) on Jul. 13, 1993 with the numbers AH64: CNCM No. 1-1333; AH65: CNCM No. 1-1334.

2. CHARACTERIZATION OF THE ANTIBODIES WHICH MAY BE USED IN A THERAPEUTIC KIT ACCORDING TO THE INVENTION

2.1. Characterization of the Inhibitory Capacity of the Anti-IL-6 Antibodies Used:

A therapeutic kit, constituted of anti-IL-6 antibodies, designed to block in vivo the biological activity of IL-6 should comprise at least one anti IL6 antibody which inhibits the biological activity of that mediator. This capacity of inhibiting IL-6 activity may be evaluated in vitro with the aid of a biological assay measuring IL-6 activity.

The biological activity of IL-6 is measured with the aid of an IL-6-dependent murine plasmacytoma line, B9, described by L. A. van Aarden (Eur. J. Immunol. 17: 1411, 1987).

This line is cultivated at 37° C. in a humidified incubator with 5% $CO_2$ (Narco incubator), in RPMI 1640 medium (reference to composition in ATCC catalog, 1988 edition, page 354), 2 mM L-glutamine, , 1 mM pyruvate, 50 IU/ml of penicillin and streptomycin, supplemented with 10% v:v fetal calf serum (Gibco) and containing 25 pg/ml of human recombinant interleukin-6 (Prepotech, Rocky Hill, N.J., USA). All products for the culture are furnished by Flow Laboratories, Scotland. The line is passaged every 48 hours; the concentration of the cell suspension is kept at below $5.10^5$ cells/ml. The actual bioassay is performed as follows: on the evening preceding the assay, the cell suspension was centrifuged, washed three times in RPMI 1640 and put back into culture at $2.10^5$ cells/ml in the same medium as before, but without IL-6. For the bioassay, the cell suspension is centrifuged, taken up in complete medium without IL-6 at $10^5$ cells/ml and added to a 96-well microtiter plate (Falcon) at 100 µl/well, i.e. $2.10^4$ cells/well. Different, measured dilutions of I1-6 in complete medium (0.5 to 50 pg/ml) or of IL-6, in the presence of the inhibitor to be tested, are added to the microtiter plate. After 48 hours of culture, 0.25 µCi of tritiated thymidine (Amersham) are added to each well and the microtiter plate is incubated for 8 hours at 37° C. Finally, the cells are precipitated onto filters with the aid of a precipitator (Skatron), the filters transferred to polypropylene tubes to which 3 ml of scintillation fluid (Amersham) are added and the radioactivity incorporated into the cell pellet is determined in a beta counter (Kontron).

A standard range for the incorporation of radioactivity, at different IL-6 dilutions, is established, the radioactivity incorporated by the cells for a given IL-6 containing a sample, or in the presence of an inhibitor of IL-6, is compared to the corresponding value of the standard range. For each point, the measurement is made using three wells. Experiment No. 1: the four antibodies utilized (AH64, AH65, BE 4, BE 8) were characterized with respect to their capacity to inhibit the proliferation of line B9, induced by Interleukin-6. The assay was done with a constant concentration of calibrated IL-6 (25 pg/ml) and different dilutions of the antibodies tested under the experimental conditions described earlier. For each antibody, the titration curve obtained permits one to measure the concentration necessary (ED 50) to inhibit the proliferation of line B9 in the presence of 25 pg/ml of IL-6 by 50%. The results are shown in table A. The four antibodies are inhibitors of the activity of IL-6. Antibody AH65 is the most effective. From the point of view of pharmacological use, any one of the three antibodies tested, might then be used, but it would be more advantageous, in order to reduce the effective dose, to include the most highly inhibitory antibody, such as AH65, in a preparation combining several anti-IL-6 antibodies.

TABLE A

| ANTIBODY | EFFECTIVE DOSE 50 ED50 (M) |
| --- | --- |
| AH65 | $3.3\ e^{-12}$ |
| AH64 | $2.3\ e^{-11}$ |
| BE8 | $1.1\ e^{-11}$ |
| BE4 | $1.2\ e^{-10}$ |

Experiment No. 2 : synergistic effect of a combination of antibody inhibitors. It was attempted to evaluate the inhibitory effect of a combination of anti-IL6 antibodies blocking the growth of the IL-6-dependent B9 line. The assay was done with a constant concentration of measured IL-6 (25 pg/ml) and different dilutions of either one of the antibodies AH64 or AH65, or of the mixture of these two antibodies in equal concentrations.

The inhibitory potential of each combination is evaluated on the basis of the total dose of antibodies inhibiting proliferation of B9 by 50%. One finds that the inhibitory dose of antibodies is lower when one employs a mixture than the dose of antibodies for each one of the antibodies constituting the mixture. Thus, the inhibitory dose of a mixture of AH65+AH64, in equal parts, is three times lower than the inhibitory dose of AH65 and twenty times lower than the inhibitory dose of AH64.

This demonstrates the synergistic effect of a combination of inhibitory antibodies. It is therefore advantageous for inhibiting the in vivo activity of IL-6 to use a combination of several inhibitory antibodies.

2.2 Definition of IL-6 Epitopes Binding Anti-IL-6 Antibody—Enzyme Immunoassay of Interleukin-6

To start, microtiter plates coated with monoclonal anti-IL-6 antibody are prepared. For this purpose, a solution of antibody against purified IL-6 (10 µg/ml in 20 mM phosphate, 0.15M NaCl, pH 7.5 buffer, designated PBS) was incubated for 24 hours at +4° C. in the wells of a 96-well polystyrene microtiter plate (Nunc). The plate is washed with the aid of an automatic washer (SLT, Salzburg); 300 µl/well of a PBS solution containing 10 g/l of bovine serum albumin (Boehringer, Mannheim) are then added for another four-hour incubation at room temperature (PBS-BSA buffer). At the same time, the different antibodies to be tested are biotinylated by reacting them with biotin-N-hydroxysuccinimide ester (Boehringer, Mannheim), according to manufacturer's instructions. The actual immunoassay was performed in the following manner:

To an anti-IL-6-coated microtiter plate are added sequentially 100 µl of either PBS-BSA buffer or of a IL-6-solution, 1 or 10 ng/ml in PBS-BSA, then 100 µl of a biotinylated antibody solution diluted to 1 mg/ml in the same buffer. In certain experiments, the biotinylated monoclonal anti-IL-6 antibody is added to a 10 µg/ml solution of a third anti-IL-6 antibody. The microtiter plate is incubated for four hours at +4° C., then washed three times with a wash solution (PBS-Tween 80, 0.05% v:v with an automatic washer (SLT). In a second step, to each well 200 µl of a solution of streptavidin linked to peroxydase (Jackson) diluted 1:10,000 in PBS/BSA was added. After a one-hour incubation at room temperature, the plate is washed as before and the binding of the avidin-peroxydase, and hence of the biotinylated antibody, is revealed in a colorimetric reaction by adding to each well 200 µl of a substrate solution containing 1 mg/ml of o-phenylenediamine dihydrochloride (Sigma) and 10 µl of $H_2O_2$ diluted to 30% in 10 ml of 0.1M, pH 4.5 phosphate-citrate buffer. The absorbance at 492 nm of each well is determined in a microtiter plate reader (SLT, Salzburg). One may conclude that two antibodies bind to distinct epitopes of IL-6, if a positive signal in the corresponding immunoassay is obtained. Finally, three antibodies can bind simultaneously to IL-6, if the presence of a third antibody does not affect the positive signal obtained with a given couple of antibodies.

Experiment No. 3 : microtiter plates coated with the four anti-IL-6 antibodies, AH65, AH64, BE8 and BE4 as well as the four corresponding biotinylated antibodies in order to test all possible combinations in an immunometric-type assay were prepared. The assay is performed according to the procedure described earlier. Results are expressed as absorbance at 492 nm for 1 ng/ml of IL-6 incubated. The four antibodies appear to fall into three groups: AH65, BE4 and an epitope common to AH64 and BE8 (table B). This result suggests that three antibodies can bind simultaneously to IL-6 : the possible combinations are AH64, AH65 and BE4 or AH65, BE4 and BE8.

TABLE B

| Tracer | Phase AH65 | Phase AH64 | Phase BE8 | Phase BE4 |
| --- | --- | --- | --- | --- |
| AH65 | — | ++ | ++ | ++ |
| AH64 | ++ | — | — | ++ |
| BE8 | ++ | — | — | ++ |
| BE4 | + | ++ | ++ | — |

++: Optical density > 1.0
+: Optical density < 1.0
—: Negative

Experiment No. 4: A second experiment was conducted to confirm that the combinations of the three independant identified antibodies could indeed bind simultaneously to IL-6. For this purpose, immunoassays were run with different pairs of compatible antibodies in the presence of a third antibody of each combination. It was observed that the signal obtained for the biotinylated pair (AH64, AH65) was not affected by the presence of antibody BE4 at 10 µg/ml. Similary, the signal obtained for the couple (BE4, BE8) is not affected by the presence of antibody AH65. One concludes from this that in the case of the two combinations AH64+AH65+BE4, on the one hand, and AH65+BE8 +BE4, on the other hand, the three antibodies can bind simultaneously to interleukin-6, defining distinct epitopes of the molecule.

3. PHARMACOKINETICS OF RADIOLABELED IL-6 IN VIVO AND THE EFFECT OF THE INJECTION OF ONE OR OF SEVERAL ANTI-IL-6 ANTIBODIES

The injection of three antibodies binding simultaneously to three distinct IL-6 epitopes prevents the stabilization and the accumulation of the target molecule in the form of immune complexes. By contrast, the injection of only one or of two antibodies stabilizes the target molecule and increases its persistence in the circulation. These experimental results demonstrate the superiority of a therapeutic kit consisting of three antibodies binding three distinct epitopes of the target molecule.

3.1 Radioactive Labeling of Interleukin-6 With $^{125}I$

Human interleukin-6 (recombinant molecule, produced in E. coli, supplied by CLB, Amsterdam) was radiolabeled by the chloramine T method, as recalled briefly hereafter: to a test tube 2 μg of IL-6 at a concentration of 100 μg/ml in pH 7.5 isotonic saline phosphate buffer (PBS buffer) and 0.5 mCi of a solution of $Na^{125}I$ (Amersham) at 100 mCi/ml are added sequentially. The reaction is then initiated by the addition of 10 μl of a solution of chloramine T (Merck) at 1 mg/ml in PBS. The reaction mixture is incubated for exactly 10 seconds at room temperature (18°–23° C.) and the reaction is terminated by the addition of 50 μl of a 10 mM solution of glycyl-tyrosine (Bachem). After a one-minute incubation the mixture is diluted in PBS buffer containing 10 g/l of bovine serum albumin (Boehringer) (PBS/BSA) to a final volume of 0.5 ml. This mixture is then fractionated by molecular sieving on a 50 cm Sephadex 650 fine (Pharmacia) column, pre-saturated in PBS-BSA. The column is eluted with PBS −0.2% BSA at a flow rate of 10 ml/hour and 2 ml fractions are collected. The radioactivity of each fraction is determined in a gamma counter (Packard) and the IL-6 concentration is determined with a commercial immunoassay (Immunotech). The fractions containing radiolabeled IL-6 are then diluted in PBS-BSA so as to obtain a solution of $3.10^7$ cpm/ml. The final specific activity is obtained by another immunobioassay of the concentration of IL-6. The specific activity always ranges from $7,5.10^6$ to $17.10^6$ cpm/pmole, i.e. from 3 to $6.10^5$ cpm/ng.

3.2 Pharmacokinetics of Radiolabeled IL-6

The in vivo pharmacokinetic experiments are carried out with 19 week-old female Balb/c mice (furnished by Charles River) and bred under standard conditions. On the evening preceding the experiment the animals are given intravenously an amount of 50 μl of the test agent diluted in sterile apyrogenic PBS-BSA. The control animals receive the isotonic solution only. On the day of the experiment, each mouse is injected intravenously with 50 μl of a radiolabeled IL-6 solution, i.e. exactly $10^6$ cpm. After a given interval of time (5, 10, 30, 60 minutes, 3, 6 and 24 hours) the animal is sacrificed and weighed with a precision balance.

Using a Pasteur pipet and following standard techniques, 1.5 ml of peripheral blood are added to a heparin-containing tube and centrifuged immediately for 5 minutes at 4000 G in a centrifuge (Jouan) so as to obtain approximately 500 μl of plasma. The animals are then dissected and the following organs taken to be analyzed: kidney, lung, heart, spleen, liver, intestin and thyroid. The radioactivity of the plasma and of each organ is determined in a gamma counter (Packard). The radioactivity taken up by each organ is ultimately expressed as percentage of total dose injected taken up per gram of organ. Finally, the plasma samples are fractionated by molecular sieving in order to identify the radioactive molecules present (see below). For each agent tested and for every time point, two animals are treated in parallel.

3.3 Molecular Sieve Chromatography

The plasma of animals injected with radiolabeled IL-6 is analyzed by fractionation on a molecular sieve column. The chromatography is carried out on a Superdex HI-load 16/60 column (Pharmacia) with a type FPLC (Pharmacia) chromatography system. A 100 μl plasma sample is applied. The column is eluted with pH 7.5 isotonic phosphate buffer at a flow rate of 2 ml/min.

1 ml fractions are collected and the radioactivity of each fraction is determined in a gamma counter (Packard). The column was pre-calibrated for molecular weights with a mixture of proteins (Pharmacia) permitting to determine the molecular weights of the components, eluted in the different fractions, to be estimated.

Figure 1B:
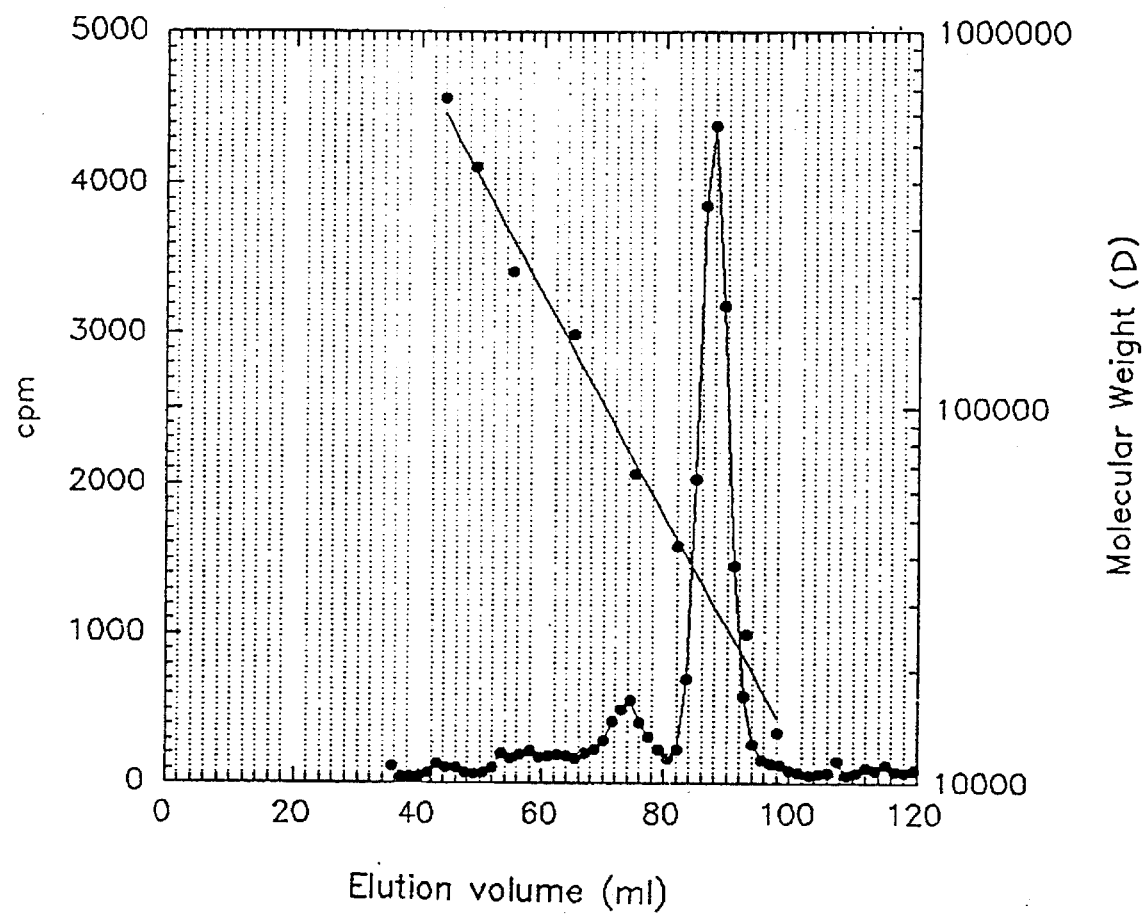
FIG. 1B shows the elution profile of a plasma sample fractionated by molecular sieving.

Experiment No. 5: the pharmacokinetics of radiolabeled human IL-6 in non-treated Balb/c mice were studied first according to the protocol described earlier (injection of 100 μl of isotonic saline solution on the evening preceding the experiment). The results are shown in FIG. 1a. The radioactivity in the plasma decreases rapidly. The half-life of the labeled molecule in the plasma may be estimated as 40–60 minutes. The parallelism of the curves showing the decrease in the different organs tested, indicates that there is no specific accumulation of the labeled molecule. A plasma sample taken 10 minutes after injection of the radiolabeled IL-6 was fractionated by molecular sieving. A major peak of radioactivity, at approximately 25 kD, appeared in the elution profile, what is in accordance with free IL-6 (FIG. 1b).

Figure 2A:
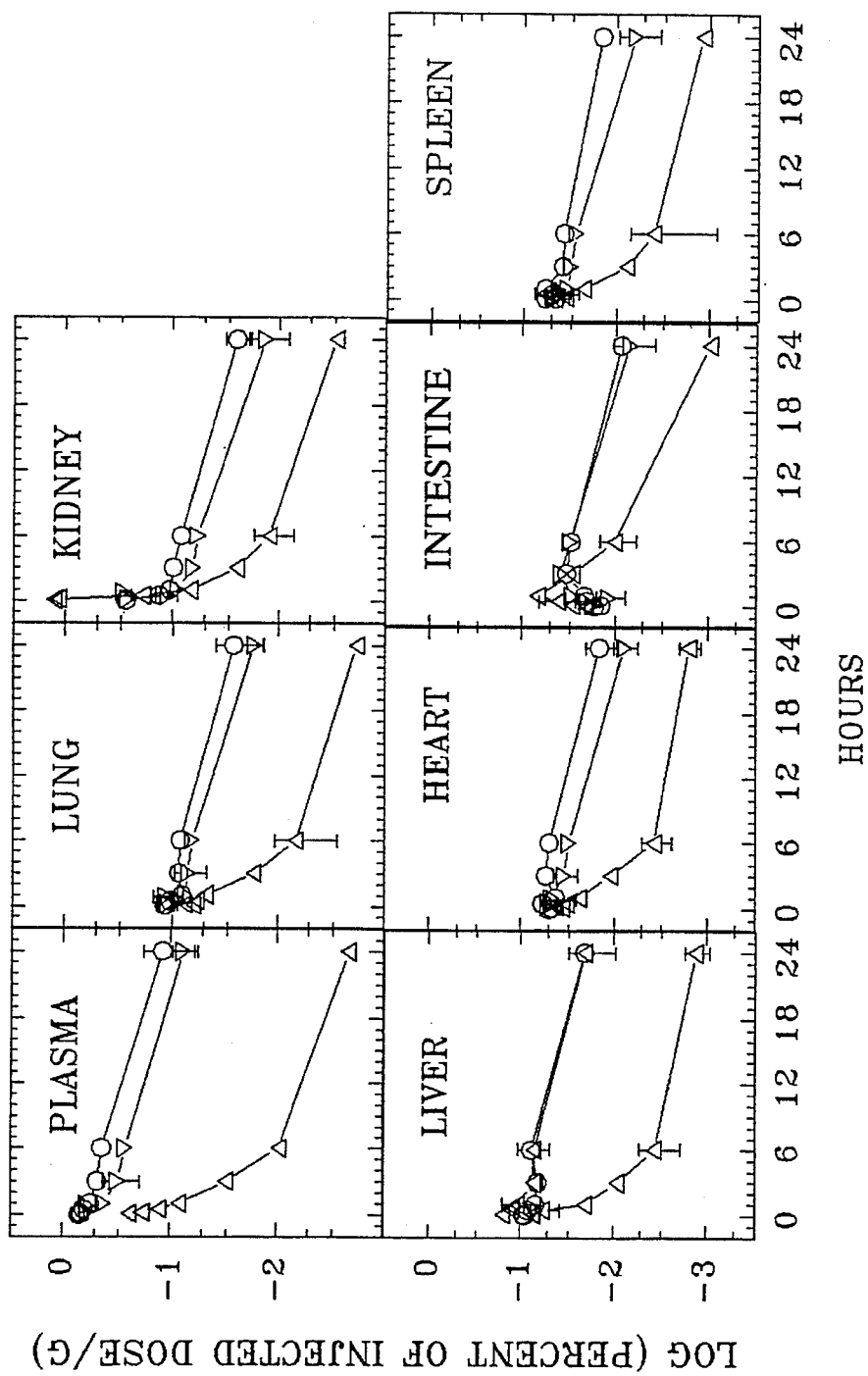
FIG. 2A shows the pharmacokinetics of radiolabeled human IL-6 in mice treated with anti-IL-6 antibody.
Figure 2B:
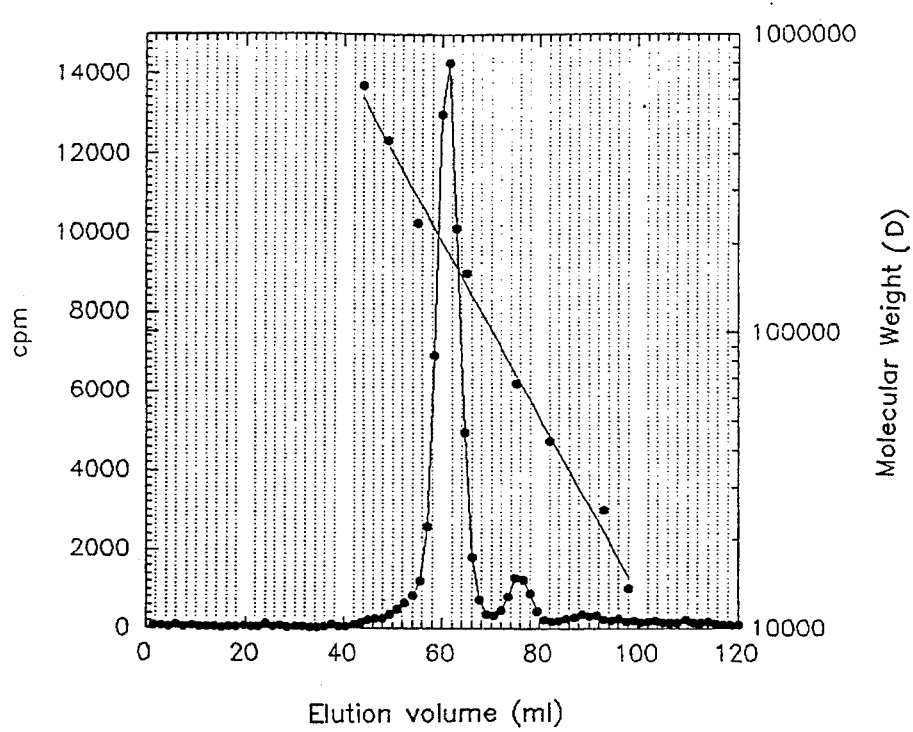
FIGS. 2B and 2C show the elution profile of plasma samples fractionated by molecular sieving for mice treated with AH65.
Figure 2C:
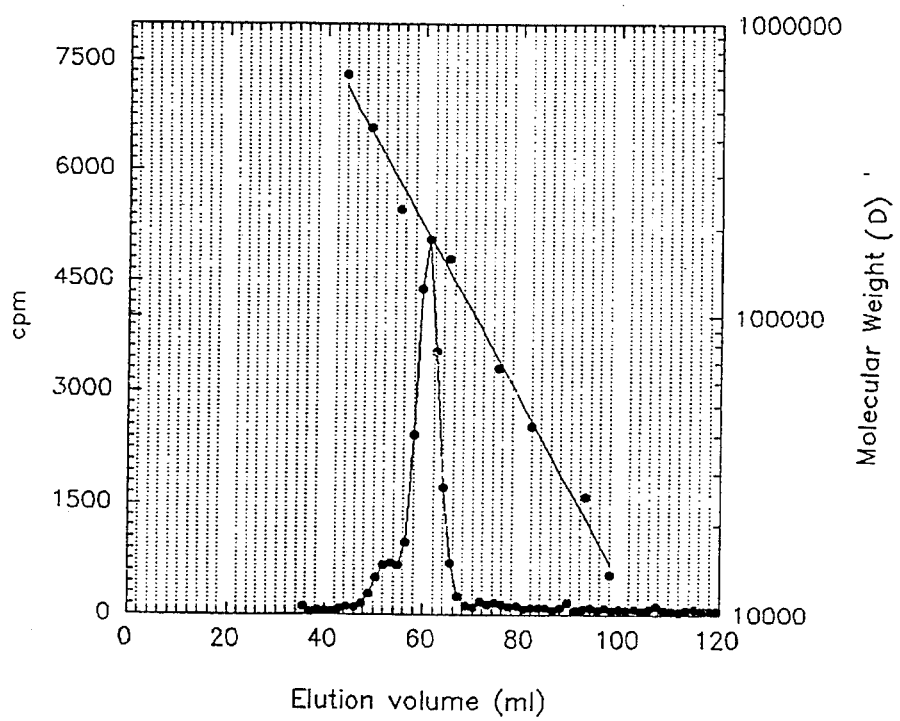

Experiment No. 6: the elimination of radiolabeled IL-6 was analyzed in mice treated with an anti-IL-6 antibody. On the evening preceding the experiment, animals were injected with 5 μg of one of the four antibodies AH64, AH65, BE4 or BE8. The pharmacokinetics of the labeled human IL-6 were studied as before. The results are shown in FIG. 2a. The radioactivity in the plasma as well as in the different organs tested, decreased much more slowly. An estimation of the half-life of the labeled molecule in the plasma is between 12 and 24 hours, depending on the anti-IL-6 antibody used. In order to confirm the nature of the radioactivity present at different time intervals after the injection of IL-6, plasma samples were fractionated by molecular sieving under the conditions described previously. By way of example, elution profiles at the 10 minute and 6 hour points for animals treated with antibody AH65, are presented in FIGS. 2b and 2c. At the two time points indicated above, the radioactivity eluted in a major peak corresponding to a molecular weight of approximately 180 Kd. This experiment confirms that the preponderant plasma form is labeled IL-6, bound to anti-IL-6 in a monovalent complex.

In animals treated with an anti-IL-6 antibody, interleukin-6 is then stabilized and accumulates in the form of immune complexes.

Experiment No. 7: the pharmacokinetics of radiolabeled IL-6 were analyzed in animals treated with combinations of several anti-IL-6 antibodies binding to different epitopes of the molecule; the following treatments were employed: AH64+AH65, BE4+BE8, AH65+BE4+BE8, AH64+AH65+ BE4 +BE8. The combination of four antibodies corresponds in fact to three distinct epitopes of the IL-6 molecule.

For each treatment, the total dose of injected antibody was 5 μg. The same amount of each antibody was employed in the different combinations: 2.5 μg for the combination of two antibodies, 1.66 μg for the combination of three antibodies, and 1.25 μg for the combination of four antibodies. The kinetics of the elimination of IL-6 was followed as above.

Figure 3A:
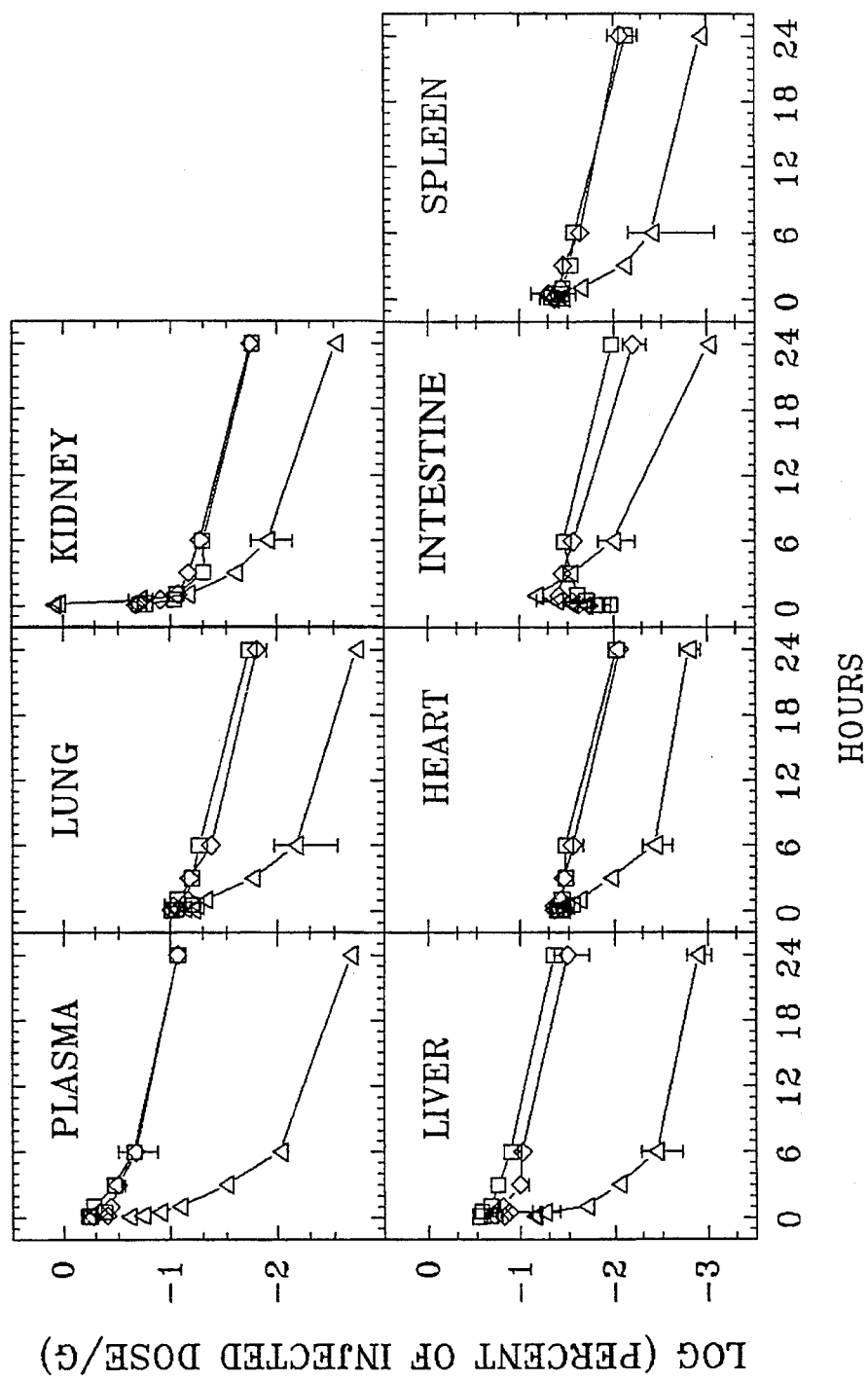
FIG. 3A shows the pharmacokinetics of radiolabeled IL-6 in treated animals.

In the case of treatment with two antibodies, the rate of elimination of the radioactivity was close to that observed in animals treated with only one monoclonal antibody. The results are similar for the two pairs of antibodies used (FIG. 3a). Molecular sieve fractionation of plasma samples taken at 15 minutes and two hours, respectively, after injection of the labeled IL-6 into animals treated with the combination AH64+AH65, shows that the divalent immune complexes (IL-6 and two antibodies) are indeed the predominant form of circulating IL-6 (see FIGS. 3b and 3c).

Figure 4A:
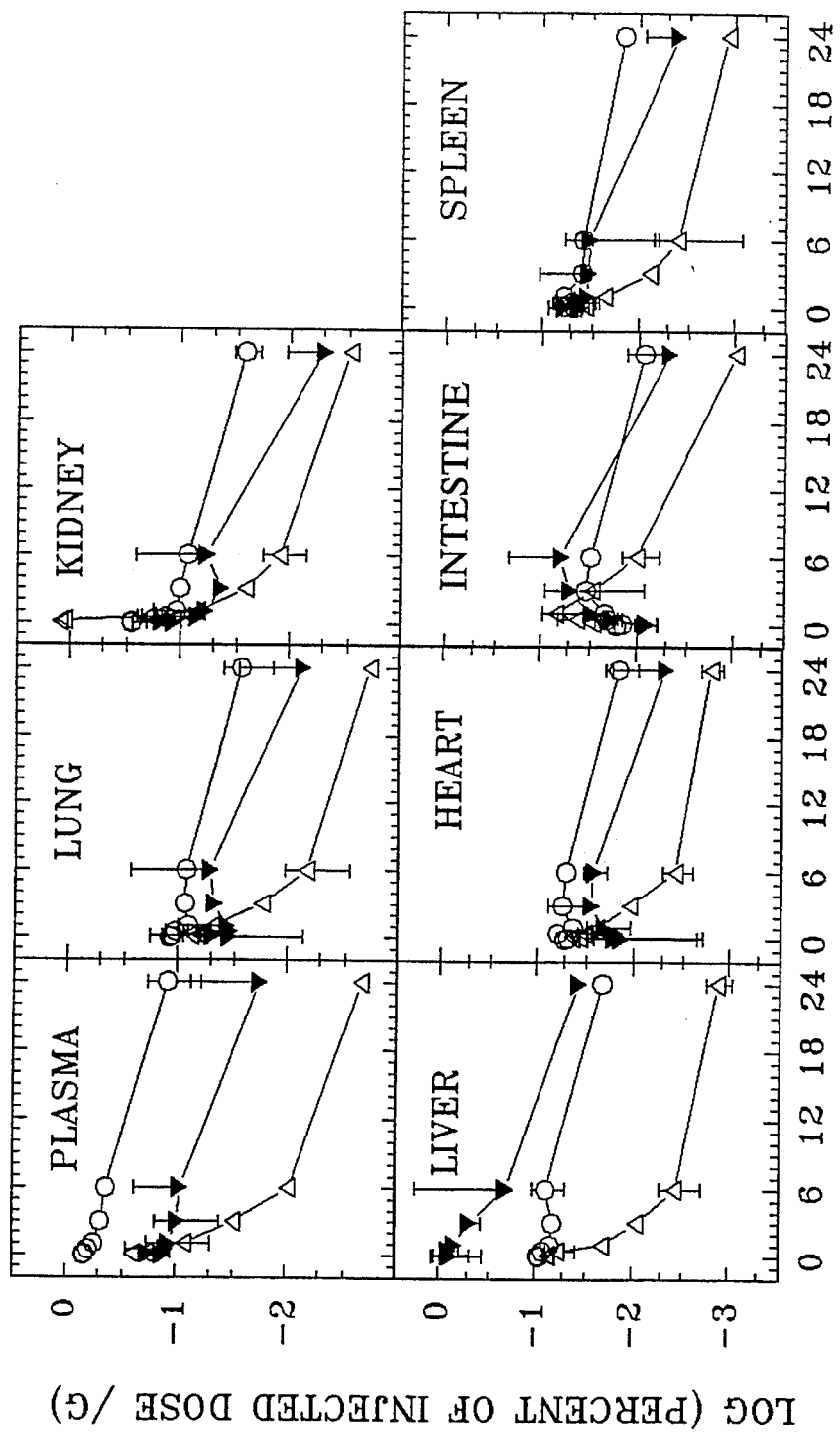
FIG. 4A shows the tissue distribution of radiolabeled IL-6.

In the case of treatment with three antibodies (such as AH65+BE4+BE8) binding to three distinct epitopes of IL-6, the initial rate of elimination of radiolabelled IL-6 is close to that of free IL-6. The analysis of the tissue distribution of the radioactivity shows a specific transitory accumulation of IL-6 in the liver, the spleen and the intestine which suggests a change in the route of elimination (see FIG. 4a). The fractionation of the plasma shows that the trivalent complexes (IL-6 and three antibodies) are eliminated immediatly. These complexes are not detectable 10 minutes after injection. The preponderant circulating forms are the monomeric and dimeric forms which confirms that the trivalent complexes are eliminated preferentially. The presence of monovalent and divalent complexes, respectively, may be explained by the partial reactivity of the tracer with the antibodies employed on the basis of the heterogeneity introduced by the iodination step (see FIGS. 4b and 4c).

Figure 5A:
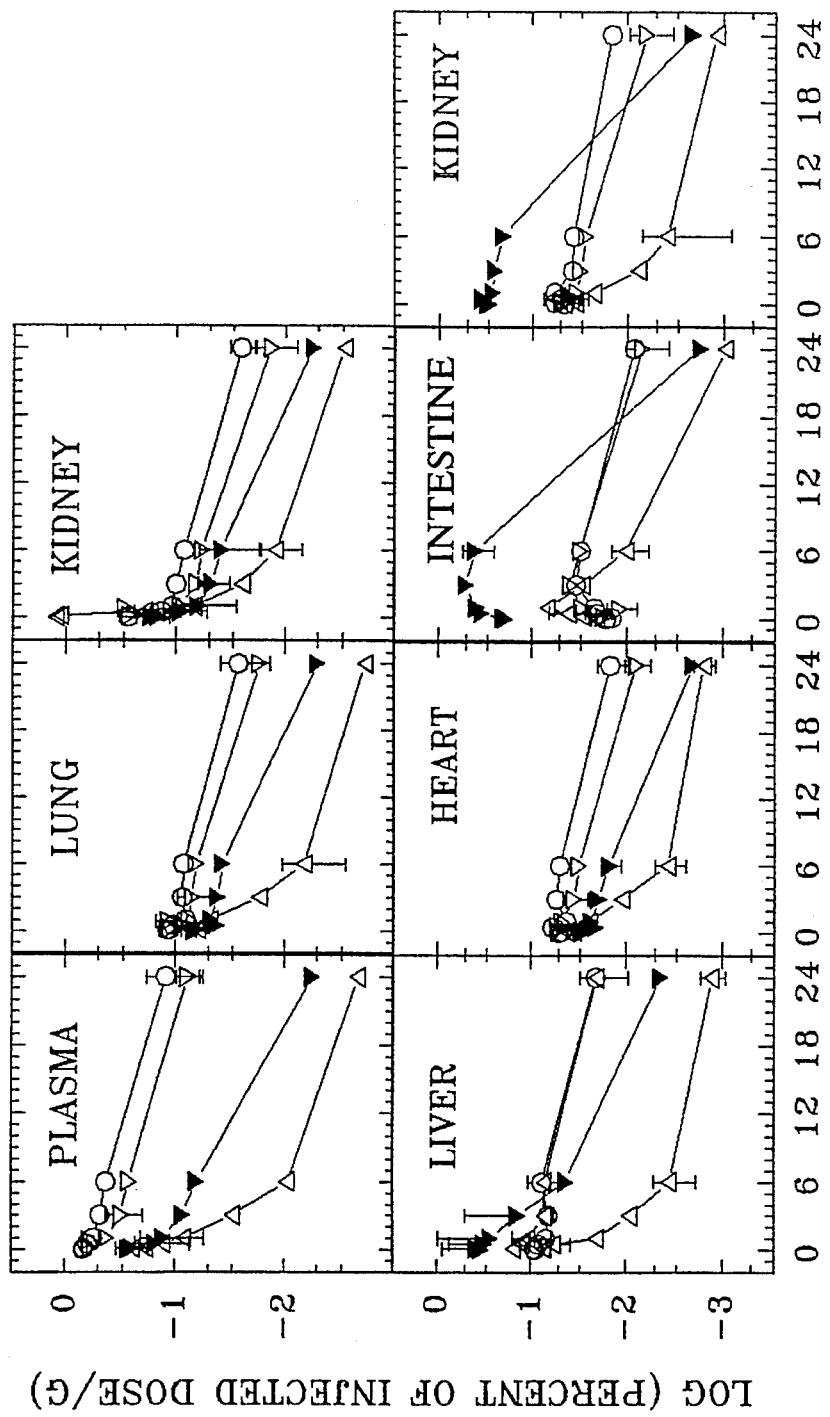
FIG. 5A shows the pharmacokinetics of radiolabeled IL-6.

In the case of treatment with the four antibodies, AH65+ AH64+BE4+BE8, only three antibodies can bind simultaneously to IL-6. The injection of this mixture must bring about the formation of two types of trivalent complexes with IL-6, one combining antibodies AH64, AH65 and BE4, the other combining with AH65, BE4 and BE8. The pharmacokinetic behavior observed is very similar to that described earlier. In particular, the initial rate of elimination of IL-6 is close to that of free IL-6. One may detect 10 minutes after injection residual trivalent complexes, which have disappeared completely one hour after injection (FIG. 5a). The fractionation of the plasma confirms the phenomenon of the preferential elimination of the trivalent complexes (FIGS. 5b and 5c).

4. PREFERENTIAL BINDING OF TRIVALENT IMMUNE COMPLEXES TO THE IMMUNOGLOBULIN RECEPTORS OF THE P388DI MONOCYTE LINE

The route of elimination and consequently the kinetics of elimination in vivo of an immune complex depend on the capacity of this complex to be recognized by the cells bearing receptors for the immunoglobulins. The trivalent immune complexes formed with IL-6 by three antibodies capable of binding to three distinct epitopes of the target molecule are able to bind preferentially to the immunoglobulin receptors. This property distinguishes the trivalent from the monovalent and divalent complexes. The experiments cited by way of example below, show the difference in pharmacodynamic behaviour which may be expected from a mixture comprising of at least three antibodies binding to three distinct epitopes for the target molecule. At the same time, the experiments furnish the basis for an in vivo assay, easy to set up, for the selection of a combination of antibodies having the properties required for in vivo utilization.

4.1 Culture of Murine Line P388 DI

The murine line P388DI, of monocyte origin, is available from the ATCC (ATCC No. TIB63). The line is maintained in continuous culture in a humidified incubator at 37° C., under 5% $CO_2$ (Narco incubator), in medium RPMI 1640, supplemented with non-essential amino acids, 2 mM glutamine, 1 mM sodium pyruvate, 50 IU/ml of penicillin, 50 IU/ml of streptomycin and fetal calf serum to a final concentration of 10% of the total volume. All these reagents were furnished by Flow Laboratories, Scotland. The line was cultivated in 250 ml culture vessels (Falcon). The cells are adherent. When the cells are at confluence, the culture is treated with a trypsin-EDTA solution (Flow) according to published procedures and the resulting cell suspension is put back into culture after a five-fold dilution. The binding experiments were done with cell suspensions obtained from cultures which had reached confluence.

4.2 Assay of Binding of Radiolabelled IL-6 by Line P388 DI Cells

First, a line P388DI cell suspension is prepared from confluent cultures by controlled treatment with trypsin. The cell suspension thus obtained is washed three times with isotonic saline phosphate (PBS) by centrifugation. The cells are taken up in an isotonic saline phosphate buffer, pH 7.5, containing 10 g/l of bovine serum albumin (Boehringer) and 5 mM sodium azide (Sigma) (designated as PBS/BSA/$N_3$ buffer) and cell density is adjusted to $1.10^6$ cells/ml. For the actual binding assay, the cell suspension is added to a round-bottomed 96-well microtiter plate (Falcon, Becton Dickinson) at 100 µl per well, i.e. $10^5$ cells per well. To each well are then added serially 150 µl of a solution of radiolabeled IL-6, diluted to $3.10^6$ cpm/ml in PBS/BSA/$N_3$ followed by 100 µl of a solution of the agent or agents to be tested, diluted in the same buffer. The mixture is incubated for two hours with shaking at 37° C. in an incubator (Narco). Radioactivity bound by the cells is then separated from free radioactivity according to a procedure described earlier (Dower S. K et al;, Biochemistry 20:6326, 1981). 150 µl of the cell suspension are taken from each well and are added to 200 µl of a mixture of phtalates (1.2 volumes of 90% dibutyl phtalate for 1 volume of 97% di (2-ethyl-hexyl) phtalate in a 500 µl polypropylene tube (Eppendorf). The tubes are centrifuged for 20 seconds at 10,000 G in a Beckman microfuge type centrifuge. After centrifugation, 50 µl of the aqueous phase which contains the free radioactivity is taken, and the tube is then cut with scissors to obtain the cell pellet which contains the bound radioactivity. The samples are then counted in a gamma counter (Packard) and results corrected for the different dilutions in order to obtain the fraction of IL-6 bound under the different conditions tested. The assay is done in duplicate for each condition.

Two experiments were performed according to the protocol described earlier (assay of binding to P388 DI. Experiment No. 8: radiolabeled IL-6 is incubated with the cell suspension in the presence of one, two, three or four anti-IL-6 antibodies. The antibodies employed in that experiment are BE4, BE8, AH64 and AH65. The total concentration of the antibodies is 3.57 µg/ml (final concentration in wells) under all conditions. When several antibodies are present, they are at the same concentration 1.8 µg/ml for each antibody, when two antibodies are present—1.2 µl/ml when three antibodies are present—0.9 µg/ml for four antibodies. The results of the experiment are shown in table C. In the absence of antibody, radiolabeled IL-6 does not bind to the cells of line P388DI. One finds that the binding of radiolabeled IL-6 is much greater in the presence of three antibodies. This effect is observed only for three antibodies capable of binding simultaneously to IL-6. Thus, when BE8, BE4, and AH64 are used, the level of binding corresponds to that observed for a combination of two antibodies, which corresponds to the competition between BE8 and AH64.

The experiment demonstrates the preferential binding to the receptors, via the constant part of the immunoglobulins, of the trivalent immune complexes.

TABLE C

| MIXTURE OF ANTIBODIES | ANTIBODIES BOUND/FREE |
| --- | --- |
| AH65 | 4.5 |
| AH64 | 5.5 |
| BE8 | 5.49 |
| BE4 | 2.91 |
| AH65/AH64 | 8.28 |
| AH65/BE8 | 9.04 |
| AH65/BE4 | 8.08 |
| AH64/BE8 | 5.32 |
| AH64/BE4 | 9.25 |
| BE8/BE4 | 13.48 |
| AH65/AH64/BE8 | 7.3 |
| AH65/AH64/BE4 | 38.8 |
| BE8/BE4/AH65 | 43.12 |
| BE8/BE4/AH64 | 12.27 |
| BE8/BE4/AH64/AH65 | 28.39 |

Experiment No. 9 : radiolabeled IL-6 is incubated with a combination of three anti-IL-6 antibodies (AH64, AH65 and BE4) at different concentrations of total antibody. Starting with a solution containing a total of 3.57 µg/ml of antibodies, i.e. 1.2 µg/ml for each anti-IL-6 antibody, a series of 1:1 dilutions down to 110 mg/ml of total antibody is made. This dilution series is tested in the P388DI binding assay. Results are shown in Table D. At all concentrations tested, the combination AH64+AH65+BE4 led to the effective precipitation of the radiolabeled IL-6.

This result indicates that the preferential binding of trivalent immune complexes occurs at low concentrations of anti-IL-6 antibodies.

TABLE D

| CONCENTRATION OF ANTIBODIES (µg/ml) | BOUND/FREE AH65/AH64/BE4 | BOUND/FREE AH65/BE4/BE8 |
| --- | --- | --- |
| 3.57 | 28.36 | 29.91 |
| 1.78 | 43.12 | 46.71 |
| 0.89 | 49.63 | 44.75 |
| 0.44 | 34.59 | 46.94 |
| 0.22 | 37.9 | 42.57 |
| 0.11 | 41.85 | 38.5 |
| 0.00 | 2.15 | 2.13 |

Example of pharmaceutical compositions:

1)—3 Vials were prepared, containing:

1 mg of lyophilized AH65 antibody 1 mg of lyophilized BE4 antibody 1 mg of lyophilized BE8 antibody —Another vial was filled with 2 ml of water for the preparation of injections.

—The 4 Vials were gathered in a box with an instruction leaflet.

2)—A Vial was prepared containing:

1 mg of lyophilized AH65 antibody 1 mg of lyophilized BE4 antibody 1 mg of lyophilized BE8 antibody —A second Vial was filled with 2 ml of water for the preparation of injections —The 2 Vials were gathered in a box with an instruction leaflet.

CONCLUSIONS

1) It is possible for a cytokine-type molecule to identify three monoclonal antibodies capable of binding simultaneously to this molecule and thus to form trivalent immune complexes. It is possible to identify the associations satisfying this criterion and including at least one antibody inhibiting the biological activity of the target molecule.

2) When a monoclonal antibody, which recognizes a cytokine type molecule, is injected into an animal, the resulting antibody-cytokine immune complexes are eliminated in the same manner as is the antibody. The residence time of the cytokine bound to the antibody being then ten times superior to that of the free cytokine. The injection of the antibody leads to the accumulation of the cytokine in the form of a monovalent immune complex, a fact which compromises the efficacy of the treatment.

3) The simultaneous injection of three anti-cytokine antibodies, recognizing three distinct epitopes, leads to the formation of complexes which are eliminated rapidly from the circulation. In this case there is no accumulation of the cytokine whose activity one attempts to inhibit. This result is obtained specifically only with trivalent complexes; the divalent complexes are eliminated like the monovalent complexes. It is thus advantageous to use an association of three antibodies, binding three distinct epitopes of a cytokine-type molecule, in order to inhibit the in vivo activity of said cytokine-type molecule.

4) The trivalent immune complexes, obtained by the reaction of a cytokine-type molecule with three antibodies recognizing distinct epitopes of that molecule, are bound preferentially by the receptors for the constant part of the immunoglobulins (FcR). This result is obtained specifically only with trivalent complexes, the divalent complexes not binding significantly to FcR. The result confirms the advantage of using in vivo a combination of three antibodies which may permit the elimination of the target molecule via the reticulohistiocytary system.

5) The use of an association of two anti-cytokine antibodies, also inhibitors, recognizing two distinct epitopes of that cytokine, allows to reduce the total quantity of antibody required to block the activity of the target molecule. It is therefore advantageous to use in vivo an association of blocking antibodies and, furthermore, in view of the results described earlier, to use an association of three antibodies recognizing three distinct epitopes of the target molecule and including at least two blocking antibodies.

6) It is of advantage for the effectiveness of the preparation that the antibodies used have a high affinity for the antigen, such that the resulting immune complexes are very stable and that the trivalent form predominates. The binding kinetics with a protein antigen in solution vary little from antibody to antibody. Conversely, the immune complexes formed may have greater or lesser stability. It is advantageous that the half-life of the antigen-antibody binding be much greater than the half-life of the antibody in circulation. This criterion is satisfied by antibodies with an affinity of above $10^9$ and preferably 10 Liter/M.

We claim:

1. A therapeutic kit for neutralizing a short life IL-6 cytokine, said cytokine being of sufficient size to comprise at least three functional antibody-binding sites, wherein said kit includes at least three unlinked individual monoclonal antibodies which have an affinity greater than $10^9$ liter/mole and bind three distinct epitopes of said cytokine, at least one of the said three monoclonal antibodies blocking the biological activity of said cytokine as evaluated in vitro with the aid of a biological assay measuring IL-6 activity.

2. The therapeutic kit, according to claim 1, wherein the monoclonal antibodies are of the IgG type.

3. The therapeutic kit, according to claim 1, wherein two of the monoclonal antibodies of the said at least three monoclonal antibodies, are capable of blocking the biological activity of said cytokine as evaluated in vitro with the aid of a biological assay measuring IL-6 activity.

4. The therapeutic kit, according to claim 1, wherein the monoclonal antibodies are partially humanized.

5. The therapeutic kit, according to claim 1, comprising the following combinations of monoclonal antibodies:

AH64, AH65 and BE4, or

AH65, BE4 and BE8, or

AH64, AH65, BE4 and BE8.

6. The process for the preparation of a kit as defined in claim 1, wherein at least three monoclonal antibodies recognizing three distinct epitopes of said IL-6 cytokine are combined, at least one of the said at least three monoclonal antibodies blocking the biological activity of said cytokine as evaluated in vitro with the aid of a biological assay measuring IL-6 activity.

7. The process according to claim 6, wherein at least three monoclonal antibodies according to the following combinations are combined:

AH64, AH65 and BE4, or

AH65, BE4 and BE8, or

AH64, AH65, BE4 and BE8.

8. The therapeutic kit, according to claim 2, wherein two of the monoclonal antibodies of the said at least three monoclonal antibodies, are capable of blocking the biological activity of said cytokine as evaluated in vitro with the aid of a biological assay measuring IL-6 activity.

9. The therapeutic kit according to claim 1, wherein said monoclonal antibodies are chimeric human-murine monoclonal antibodies comprising an antigen-binding domain of murine origin and an Fc fragment of human origin.

10. The therapeutic kit according to claim 2, wherein said monoclonal antibodies are chimeric human-murine monoclonal antibodies comprising an antigen-binding domain of murine origin and an Fc fragment of human origin.

* * * * *